United States Patent [19]
Zimmerman

[11] Patent Number: 6,025,389
[45] Date of Patent: *Feb. 15, 2000

[54] PHARMACEUTICAL AND VETERINARY COMPOSITIONS OF MUPIROCIN AND METHODS FOR THEIR PREPARATION

[75] Inventor: Harvey Lee Zimmerman, Bristol, Tenn.

[73] Assignee: SmithKline Beecham Corporation, Philadelphia, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/903,255

[22] Filed: Jul. 25, 1997

Related U.S. Application Data

[63] Continuation of application No. 08/535,089, filed as application No. PCT/US94/12026, Oct. 20, 1994, abandoned.

[30] Foreign Application Priority Data

Oct. 22, 1993 [GB] United Kingdom .................... 9321876
Oct. 29, 1993 [GB] United Kingdom .................... 9322288

[51] Int. Cl.$^7$ ............................. A01N 43/16; A61K 31/35
[52] U.S. Cl. ............................................. 514/460; 514/969
[58] Field of Search ...................... 514/460, 969

[56] References Cited

U.S. PATENT DOCUMENTS

| | | | |
|---|---|---|---|
| 3,758,686 | 9/1973 | Sieger et al. | 424/241 |
| 4,790,989 | 12/1988 | Hunter et al. | |
| 4,847,068 | 7/1989 | Dole et al. | 424/47 |
| 4,879,287 | 11/1989 | Orr et al. | 514/171 |

FOREIGN PATENT DOCUMENTS

| | | |
|---|---|---|
| 069423 | 1/1983 | European Pat. Off. |
| 251434 | 1/1988 | European Pat. Off. |

OTHER PUBLICATIONS

Remington's Pharmaceutical Sciences, pp. 1242–1246, 1975.

*Primary Examiner*—Rebecca Cook
*Attorney, Agent, or Firm*—Elizabeth J. Hecht; Stuart R. Suter; William T. King

[57] ABSTRACT

The invention is directed to a pharmaceutical composition comprising a cream base which comprises mupiricin dihydrate, a mineral oil, one or more fatty alcohols or fatty esters, a polyoxyethylene ether or ester surfactant, xanthan gum, water and a method for treating a bacterial infection using said composition.

4 Claims, No Drawings

PHARMACEUTICAL AND VETERINARY COMPOSITIONS OF MUPIROCIN AND METHODS FOR THEIR PREPARATION

This is a continuation Ser. No. 08/535,089, filed Jun. 6, 1995 abandoned, which is a 371 of PCT/US94/12026 filed Oct. 20, 1994.

This invention is concerned with novel compositions for use as carriers for therapeutic compounds. In particular it is concerned with so-called "creams" used as vehicle for topical application of active therapeutic agents, such as antibiotics.

EP-A-0 069 423 (Gist-Brocades) discloses so-called "fatty-creams" for pharmaceutical topical compositions which comprise from 50 to 80% by weight of fatty materials, 1.5 to 5% by weight of hydrophilic, non-ionic surfactant and a therapeutic agent. Preferred compositions comprise cetyl stearyl alcohol, liquid paraffin, white soft paraffin and cetomacrogol 1000.

EP-A-0 251 434 (Beecham Group) discloses inter alia various cream formulations containing the antibiotic mupirocin. One embodiment comprises 1 to 3% by weight of mupirocin (or a salt thereof), 25 to 60% by weight of liquid paraffin, 20 to 50% by weight of water and 3 to 30% by weight of emulsifier. Example 6 thereof discloses a cream comprising liquid paraffin (42%), stearyl alcohol (16.4%) and cetomacrogol 1000 (3.6%).

Topical antibacterial compositions comprising mupirocin are marketed in the UK by Beecham Research Laboratories under the trade names Bactroban Ointment and Bactroban Nasal. The first product is an ointment comprising a water soluble polyethylene glycol base whilst the second product comprises the calcium salt of mupirocin in a white soft paraffin based ointment containing a glycerin ester.

Within the broad range of compositions disclosed by the above prior art, we have now discovered a narrow band of formulations that exhibit improved cosmetic properties over the prior art formulations.

According to the present invention there is provided a pharmaceutical or veterinary composition comprising a cream base and a therapeutic agent characterised in that the cream base comprises:

45 to 60%, preferably 50 to 55% by weight of a mineral oil;

5 to 15%, preferably 5 to 10% by weight of one or more fatty alcohols or fatty esters;

4 to 8%, preferably 5 to 7% by weight of a polyoxyethylene ether or ester surfactant; and 20 to 35%, preferably 25 to 35% by weight of water.

The percentages in the above composition are based on the total weight of the composition which typically also contains from 1 to 3% by weight of a therapeutic agent, such as an antibiotic.

Suitably, the mineral oil and fatty alcohol or ester together compromise from 50 to 75%, preferably 55 to 70%, more preferably from 55 to 65%, by weight of the comprise. Suitably, the ratio of mineral oil to fatty alcohol or ester is in the range of from 1:3 to 1:12, prefreably from 1:5 to 1:11, by weight.

The therapeutic agent may be any such agent which is effective in topical application. As an antibiotic suitable for topical use there may be mentioned in particular mupirocin, especially its calcium salt, in particular, the dihydrate thereof. Suitably, mupirocin or a salt thereof is present in from 1 to 3% by weight of the formulation, typically about 2% (expressed as the weight of the free acid).

The term "mineral oil" as used herein includes any that is suitable for use in a topical pharmaceutical or veterinary composition and includes mineral oil USP, light mineral oil NF, liquid paraffin BP and light liquid paraffin BP. The mineral oil known as mineral oil USP is especially suitable.

As fatty alcohol or ester there may be used any of such materials conventionally used in pharmaceutical or veterinary compositions such as stearyl alcohol, cetyl alcohol, cetyl stearyl alcohol, myristyl alcohol and glycerin monostearate. Suitably, a mixture of stearyl alcohol and cetyl alcohol is used.

The polyoxyethylene ester or alcohol used in this invention is one which will function as a non-ionic surfactant. As indicated in EP-A-0 069 423 cited above, it may be advantageous for the surfactant to have an BLB value of 14 or above. Suitable materials include polyoxyethylene glycol monocetyl ethers, such as the material sold under the trade name Cetomacrogol 1000, and polyoxyethlene sorbitan monostearates, such as the material sold under the trade name Polysorbate 60, or polyoxyethylene sorbitan monoleates, as sold under the trade name Tween 80.

The composition of this invention may also include minor amounts of conventional additives such as viscosity modifiers, for example xanthan gum, and preservatives, such as phenoxyethanol or benzyl alcohol, including mixtures thereof. Also for some therapeutic agents it may be necessary to incorporate buffering agents to maintain a suitable pH.

Preferred compositions within the present invention comprise from 50 to 55% by weight of a mineral oil, suitably mineral oil USP; from 5 to 10% by weight of a fatty alcohol or ester, suitably cetyl alcohol or stearyl alcohol or a mixture thereof; from 5 to 7% of a polyoxyethylene ether or ester surfactant, suitably a polyethylene glycol monocetyl ether such as cetomacrogol 1000; from 25 to 35% by weight of water and from 1 to 3%, suitably about 2% by weight (expressed as the weight of free acid) of the calcium salt of mupirocin, in particular the dihydrate salt thereof.

The cream base may be prepared by conventional techniques well known to those skilled in the art. Generally, a suitable process comprises admixing the various ingredients of the cream in appropriate relative amounts in any order that is convenient and thereafter, and if necessary, adjusting the pH to the final desired value. For example, the components of the base may be mixed together at an elevated temperature, for example 60–70° C., until an emulsion has forned. The therapeutic agent may be added after cooling the emulsified cream base, or during mixing, if it is stable to the temperatures employed.

Compositions of the invention are intended for pharmaceutical or veterinary use. Compositions may optionally be provided in sterile condition, by incorporating a conventional sterilisation step into the above procedure. Alternatively, sterile ingredients may be mixed under aseptic conditions.

In a further aspect, the present invention provides pharmaceutical or veterinary compositions for use in therapy.

In addition, in another aspect of this invention, the cream base per se as described may be used as a moisturising cream or emollient without the presence of a therapeutic agent.

The following examples illustrate compositions in accordance with the invention:

|  | % by wt |
|---|---|
| Example 1 | |
| Mineral Oil USP | 54.9 |
| Polyethylene glycol (1000) monocetyl ether* | 5.0 |
| Stearyl Alcohol NF | 3.5 |
| Cetyl Alcohol NF | 3.5 |
| Phenoxyethanol | 0.5 |
| Calcium Mupirocin | 2.4 |
| Xanthan Gum | 0.2 |
| Purified Water | 30.0 |
| Example 2 | |
| Mineral Oil USP | 51.9 |
| Polyethylene glycol (1000) monocetyl ether | 6.0 |
| Stearyl Alcohol NF | 3.5 |
| Cetyl Alcohol NF | 3.5 |
| Phenoxyethanol | 0.5 |
| Benzyl Alcohol | 1.0 |
| Calcium Mupirocin | 2.4 |
| Xanthan Gum | 0.2 |
| Purified Water | 31.0 |
| Example 3 | |
| Mineral Oil USP | 50.9 |
| Polyethylene glycol (1000) monocetyl ether | 6.0 |
| Stearyl Alcohol NF | 3.5 |
| Cetyl Alcohol NF | 3.5 |
| Phenoxyethanol | 0.5 |
| Benzyl Alcohol | 1.0 |
| Calcium Mupirocin | 2.4 |
| Xanthan Gum | 0.2 |
| Purified Water | 32.0 |

*Cetomacrogol 1000

I claim:

1. A pharmaceutical or veterinary composition comprising about 2.4% by weight of calcium mupirocin; about 50.9% by weight mineral oil USP; about 6% by weight polyethylene glycol monocetyl ether; about 3.5% by weight stearyl alcohol; about 3.5% by weight cetyl alcohol; about 0.5% by weight phenoxyethanol; about 1% by weight benzyl alcohol; about 0.2% by weight xanthan gum; and about 32% by weight purified water.

2. A method of treating bacterial infection, comprising the step of applying to a subject in need thereof a therapeutically effective amount of the composition as claimed in claim 1.

3. The composition as claimed in claim 1, wherein the calcium mupirocin is calcium mupirocin dihydrate.

4. A method of treating bacterial infection, comprising the step of applying to a subject in need thereof a therapeutically effective amount of the composition as claimed in claim 3.

* * * * *